US 8,403,833 B2

(12) United States Patent
Umemoto

(10) Patent No.: US 8,403,833 B2
(45) Date of Patent: Mar. 26, 2013

(54) MEDICAL APPARATUS

(75) Inventor: Yoshitaka Umemoto, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 155 days.

(21) Appl. No.: 13/088,750

(22) Filed: Apr. 18, 2011

(65) Prior Publication Data

US 2011/0282154 A1   Nov. 17, 2011

Related U.S. Application Data

(63) Continuation of application No. PCT/JP2010/069829, filed on Nov. 8, 2010.

(30) Foreign Application Priority Data

Nov. 18, 2009   (JP) .................................. 2009-263175

(51) Int. Cl.
  *A61B 1/00* (2006.01)
(52) U.S. Cl. .......................... 600/149; 600/145; 600/146
(58) Field of Classification Search .................. 600/106, 600/145, 146, 149; 606/1
  See application file for complete search history.

(56) References Cited

U.S. PATENT DOCUMENTS

| 7,348,751 | B2 | 3/2008 | Kawai et al. | |
| 7,981,028 | B2* | 7/2011 | Kawai et al. | 600/145 |
| 2004/0138530 | A1 | 7/2004 | Kawai et al. | |
| 2008/0262306 | A1* | 10/2008 | Kawai | 600/118 |
| 2011/0009698 | A1* | 1/2011 | Ashida et al. | 600/118 |

FOREIGN PATENT DOCUMENTS

| EP | 1 464 270 A1 | 10/2004 |
| JP | 06-022904 | 2/1994 |
| JP | 2000-300511 | 10/2000 |
| JP | 2004-041538 | 2/2004 |
| JP | 2007-054307 | 3/2007 |
| JP | 2007-283115 | 11/2007 |

* cited by examiner

*Primary Examiner* — John P Leubecker
(74) *Attorney, Agent, or Firm* — Scully, Scott, Murphy & Presser, P.C.

(57) ABSTRACT

A medical apparatus includes a bending portion that is bent via a pulled wire, a drive section that pulls the wire, a detection section and a drive force amount detection section that detect an amount of drive of the drive section and an amount of drive force, a storage section that stores information on a correlation of the amount of drive force and the amount of drive of the drive section beforehand, a bending amount detection section that detects the amount of bending of the bending portion based on the amount of drive and the amount of drive force, and the information of the storage section, a judgment section that judges the presence or absence of looseness of the wire from a detection result of the drive force amount detection section and a correction section that corrects the amount of drive by the drive section based on a judgment result of the judgment section.

20 Claims, 10 Drawing Sheets

MEDICAL APPARATUS

CROSS REFERENCE TO RELATED APPLICATION

This application is a continuation application of PCT/JP2010/069829 filed on Nov. 8, 2010 and claims benefit of Japanese Application No. 2009-263175 filed in Japan on Nov. 18, 2009, the entire contents of which are incorporated herein by this reference.

BACKGROUND OF THE INVENTION

1. Field of the Invention

The present invention relates to a medical apparatus that electrically drives bending of a bending portion.

2. Description of the Related Art

Various medical apparatuses provided with a bending portion which can be bent have been developed in recent years. For example, an endoscope or treatment instrument provided with a bending portion on a distal end side of an insertion portion which is inserted into a body is widely used in a medical field.

Furthermore, treatment on a lesioned region or the like in the body is performed using a treatment instrument inserted into a treatment instrument channel provided in an endoscope.

Furthermore, treatment may also be performed under observation through an endoscope using a treatment instrument without using any treatment instrument channel.

Furthermore, to improve operability, an active treatment instrument or the like provided with drive means (actuator) to electrically drive a bending portion is commercialized. The medical apparatus such as the active treatment instrument provided with the bending portion on its distal end side adopts a configuration in which the bending portion and the drive means are connected via an angle wire (hereinafter abbreviated as "wire"), the wire is pulled by drive means provided on the operator's hand side so as to drive the bending portion on the distal end side.

In such a configuration, it is structurally difficult to completely avoid looseness in the wire inserted into a flexible and elongated axial portion between the bending portion and the drive means on the operator's hand side so as to enable the wire to be inserted into the body cavity in a bent state. Moreover, the looseness may cause discrepancy between the amount of drive of the drive means on the operator's hand side and the amount of operation of the bending portion on the distal end side.

For this reason, an endoscope disclosed in Japanese Patent Application Laid-Open Publication No. 2000-300511 as a first prior art provides a tension sensor that detects tension acting on the wire to remove looseness of the wire and controls looseness using tension information detected by the tension sensor.

Furthermore, as a second prior art, Japanese Patent Application Laid-Open Publication No. 2007-283115 discloses a control apparatus that removes looseness of a wire whenever the wire is loose to improve the response to an operation command for driving the bending of a bending portion.

SUMMARY OF THE INVENTION

A medical apparatus according to one aspect of the present invention includes a bending portion that is bent via a pulled wire, a drive section that generates an amount of drive force to pull the wire, a detection section for detecting an amount of drive of the drive section, a drive force amount detection section that detects an amount of drive force of the drive section, a storage section that stores information on a correlation of the amount of drive force and the amount of drive of the drive section with respect to an amount of bending of the bending portion beforehand, a bending amount detection section that detects the amount of bending of the bending portion based on the amount of drive and the amount of drive force, and the information stored in the storage section, a judgment section that judges the presence or absence of looseness of the wire from a detection result of the drive force amount detection section and a correction section that corrects the amount of drive by the drive section based on a judgment result of the judgment section.

DETAILED DESCRIPTION OF THE PREFERRED EMBODIMENT(S)

Hereinafter, embodiments of the present invention will be described with reference to the accompanying drawings.

First Embodiment

Figure 1:
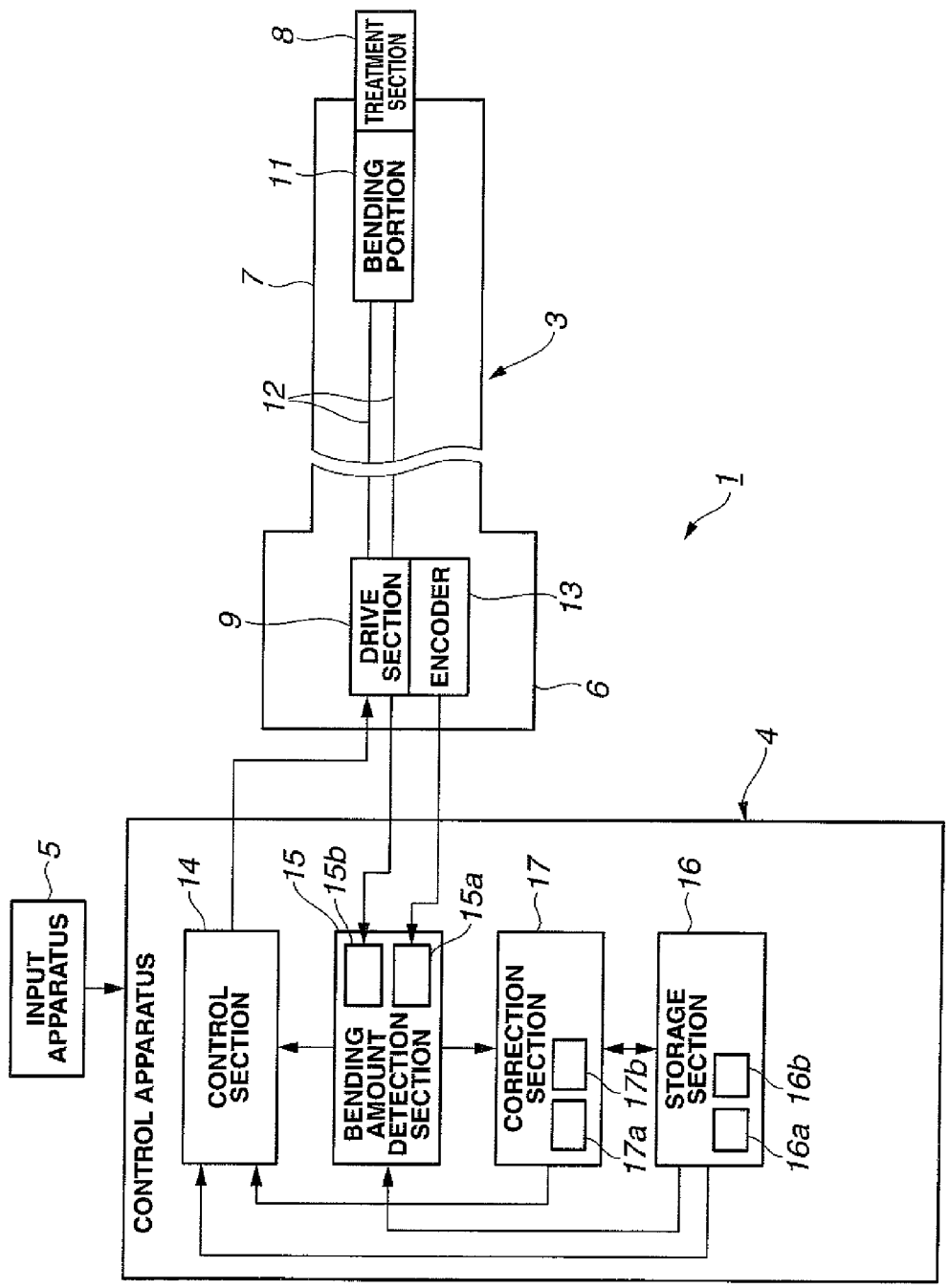
FIG. 1 is a block diagram illustrating a configuration of a treatment instrument apparatus according to a first embodiment of the present invention.

A treatment instrument apparatus 1 according to a first embodiment of a medical apparatus of the present invention as shown in FIG. 1 is provided with an active treatment instrument (hereinafter, simply referred to as "treatment instrument") 3 used by being inserted into a treatment instrument channel (hereinafter referred to as "channel") 39 of an endoscope 2 which is inserted, for example, into a body cavity shown in FIG. 2 to actively drive the bending of a bending portion 11.

Furthermore, the treatment instrument apparatus 1 is provided with a control apparatus 4 connected to the treatment instrument 3 to control the treatment instrument 3 and an input apparatus 5 connected to the control apparatus 4 for an operator to perform a command input operation. In the example shown in FIG. 2, the input apparatus 5 is made up of a joystick apparatus 5a provided at a grasping portion 6 at a rear end of the treatment instrument 3.

The treatment instrument 3 includes an elongated and flexible axial section 7 inserted into the channel 39, a treatment section 8 provided at a distal end of the axial section 7 for performing treatment, and a drive section 9 provided at a rear end of the axial section 7. In FIG. 2, the treatment section 8 is made up of a biopsy needle punctured into, for example, a diseased part to pick up a living tissue. Furthermore, in FIG. 2, the drive section 9 is provided inside the grasping portion 6.

The bendable bending portion 11 is provided at a rear end position of the treatment section 8 as an active mechanism and the bending portion 11 is connected to the drive section 9 as drive means for generating an amount of drive force via angle wires (simply abbreviated as "wire") 12 for causing the bending portion 11 to bend. The drive section 9 drives the bending of the bending portion 11 toward the pulled wire 12 side by pulling one of the pair of wires 12 and loosening the other according to the amount of drive force generated.

The drive section 9 is provided with an encoder 13 as detecting means for detecting a drive position of the drive section 9 (and for detecting the amount of drive thereof). The encoder 13 is made up of a rotary encoder, a potentiometer or the like.

The control apparatus 4 includes a drive section control section (simply abbreviated as "control section") 14 having a function of driving the drive section 9 and a bending amount detection section 15 as bending amount detecting means for detecting the amount of bending (bending angle) of the bending portion 11 based on the amount of drive and the amount of drive force by a detection signal of the drive position of the drive section 9 outputted from the encoder 13.

The bending amount detection section 15 detects the amount of bending of the bending portion 11 with reference to information stored in storing means, which will be described below. That is, the bending amount detection section 15 detects the bending angle of the bending portion 11 through estimation with reference to the information stored in the storing means beforehand, and can therefore be said to be a bending amount estimation section.

The bending amount detection section 15 includes a drive amount detection section 15a that detects the amount of drive (amount of operation) of the drive section 9 from the detection signal of the encoder 13 and a drive force amount detection section 15b as drive force amount detecting means for detecting the amount of drive force of the drive section 9 from a drive signal (to be more specific, a current value, for example) for driving the drive section 9.

As will be described later, since the drive section 9 is made up of a motor in the present embodiment, the encoder 13 generates a detection signal of rotation position or angle of rotation of the motor and the drive amount detection section 15a as the drive amount detecting means detects the angle of rotation of the motor as the amount of drive.

Furthermore, the control apparatus 4 includes a storage section 16 as storing means for storing information such as operation characteristics or operation parameters for the drive section 9 to bend the bending portion 11 provided on the distal end side of the axial section 7.

Furthermore, the control apparatus 4 includes a correction section 17 that performs, when the drive section 9 drives the bending portion 11, drive control so as to remove looseness of the wire 12 with reference to the information of the storage section 16 and corrects the drive by the drive section 9 because the operation state (operation characteristics) varies due to (before and after removal of) looseness, or to be more specific, corrects the operation state (operation characteristics) of the drive section 9 as correction means.

The storage section 16 includes an operation characteristic storage section 16a that stores, in advance, information on operation characteristics or operation parameters (of bending drive) of the drive section 9 that drives the bending of the bending portion 11 by pulling or loosening the wires 12 and the bending portion 11 that is driven to bend.

The operation characteristic storage section 16a stores, in advance, information on a correlation of the amount of drive force (output torque of the motor) and the amount of drive (angle of rotation) of the drive section 9 with respect to the bending angle of the bending portion 11.

Therefore, the information on the operation characteristics stored in the operation characteristic storage section 16a includes information on a correlation between the angle of rotation of the motor based on the detection signal of the encoder 13 and the corresponding bending angle of the bending portion 11 and also information on a correlation between the output torque of the motor (hereinafter, simply referred to as "torque") and the corresponding bending angle of the bending portion 11.

Furthermore, the storage section 16 is provided with a state storage section 16b that stores an operation state (to be more specific, torque and angle of rotation of the motor at each time) of the drive section 9 when the drive section 9 drives the bending of the bending portion 11 and the corresponding bending angle of the bending portion 11 on a time-series basis (chronologically).

The operator inputs a command on a bending angle for bending the bending portion 11 from the input apparatus 5 and the bending angle inputted as a command is thereby inputted to the control section 14 as a command value.

The control section 14 reads the information of the operation characteristic storage section 16a of the storage section 16, outputs a drive signal to drive the motor making up the drive section 9 so as to obtain the output torque and the angle of rotation corresponding to the bending angle as the command value with reference to the information and drives the bending of the bending portion 11 so as to obtain the bending angle as the command value via the wires 12.

Furthermore, the correction section 17 includes a judgment section 17a that temporally monitors the detection result of the amount of drive force of the drive force amount detection section 15b and thereby judges whether or not looseness occurs in the wire 12, that is, the presence or absence of looseness. Furthermore, the correction section 17 also includes a comparison section 17b that compares the detection result of the drive force amount detection section 15b and information (to be more specific, threshold of torque) for judging the presence or absence of looseness. The information (threshold of torque) for judging the presence or absence of looseness is stored, for example, in the storage section 16 beforehand.

The judgment section 17a judges the presence or absence of looseness according to the comparison result of the comparison section 17b. When the judgment section 17a judges that looseness is present, the correction section 17 controls the drive of the drive section 9 via the control section 14 so as to remove the looseness of the wires 12. The judgment section 17a may also be configured to include the comparison section 17b.

When looseness is present, the angle of rotation is different from that set when looseness is not present, and therefore the correction section 17 corrects the drive of the drive means (to be more specific, corrects the angle of rotation).

Furthermore, the correction section 17 controls the information on the operation state of the drive section 9 and the bending angle of the bending portion 11 so as to be stored in the state storage section 16b of the storage section 16 on a time-series basis. By storing the information on the operation state on a time-series basis in this way, it is possible to accurately manage the operation state of the drive section 9 and the state of the bending angle of the bending portion 11 in association with each other at each time and accurately drive the bending of the bending portion 11.

The block configuration in FIG. 1 shows one configuration example of the function block and the present invention is not limited to the illustrated configuration example. For example, the control section 14 may also be configured to include the functions of the bending amount detection section 15 and the correction section 17.

Figure 3:
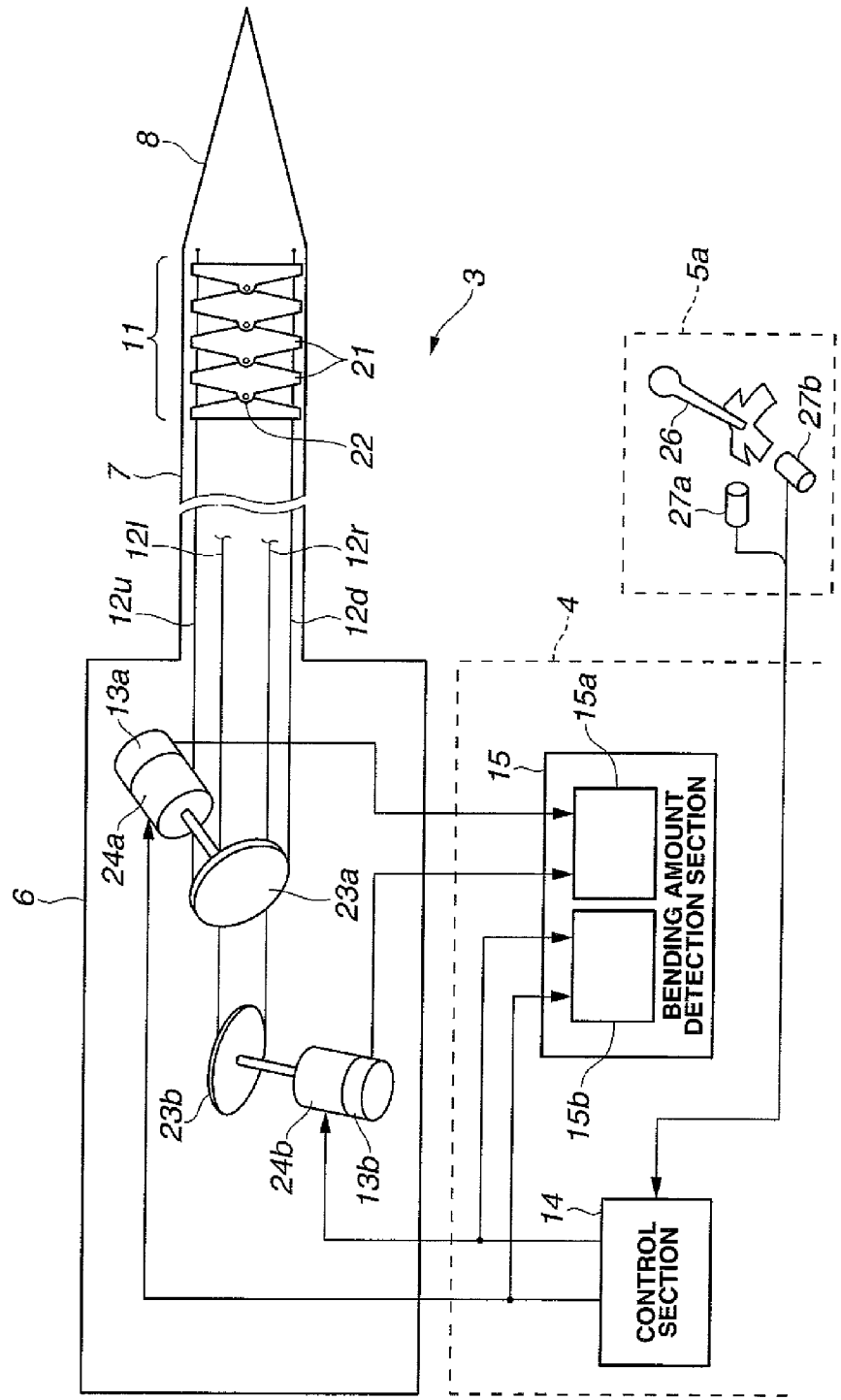
FIG. 3 is a diagram illustrating a schematic configuration of the treatment instrument.

FIG. 3 illustrates a specific configuration example of the treatment instrument 3. As shown in FIG. 3, a biopsy needle using puncturing is formed at the distal end of the axial section 7 as the treatment section 8. The bending portion 11 is formed at a rear end of the biopsy needle in which a plurality of quasi-ring-shape bending pieces 21 are pivotably connected to each other in the longitudinal direction of the axial section 7, with neighboring pieces thereof tied together by riveted portions 22.

The bending direction of each bending piece 21 is determined by the position at which the rivet 22 is provided, and the rivets 22 are arranged alternately or cyclically in horizontal and vertical positions as appropriate, and the bending pieces 21 are enabled to bend in the vertical and horizontal directions.

FIG. 3 is a simplified view showing only the rivets 22 to be bent in the vertical direction. Furthermore, wires $12u$, $12d$, and $12l$, $12r$ for bending in the vertical and horizontal directions are inserted into the axial section 7 and the distal ends of the wires $12u$, $12d$, and $12l$, $12r$ are fixed to the treatment section 8.

Furthermore, the rear ends of the wires $12u$, $12d$, and $12l$, $12r$ are looped over a vertical bending pulley $13a$ and a horizontal bending pulley $13b$ disposed in the grasping portion 6 whose diameter is extended at the rear end of the axial section 7.

The centers of rotation of pulleys $23a$ and $23b$ are connected to axes of rotation of electric motors (hereinafter, simply referred to as "motors") $24a$ and $24b$ respectively and the motors $24a$ and $24b$ are freely rotated forward or backward according to a drive signal from the control section 14.

Concurrently with the rotations of the motors $24a$ and $24b$, the pulleys $23a$ and $23b$ also rotate and the wires $12u$, $12d$, and $12l$, $12r$ looped over the pulleys $23a$ and $23b$ are pulled and loosened respectively. The bending portion 11 is then driven to bend in the direction of the pulled wire. That is, the drive means for electrically driving the bending of the bending portion 11 is made up of the motors $24a$ and $24b$, and the pulleys $23a$ and $23b$.

Drive signals for driving the motors $24a$ and $24b$ are inputted to the drive force amount detection section $15b$ that detects torque T as the amount of drive force of the motors $24a$ and $24b$. The drive force amount detection section $15b$ detects the torque T as the amount of drive force for driving the bending of the bending portion 11 from electric characteristics of the motors $24a$ and $24b$ and current values of the drive signals via the wires $12u$, $12d$, $12l$ and $12r$.

FIG. 1 shows a configuration in which the grasping portion 6 and the control apparatus 4 are connected together via a cable, but a configuration may also be adopted in which the control apparatus 4 is provided inside the grasping portion 6.

When the pulleys $23a$ and $23b$ are rotated, the amounts of pulling of the wires $12u$, $12d$, $12l$ and $12r$ are determined in association with the amounts of rotation (angles of rotation) of the pulleys $23a$ and $23b$, and the bending portion 11 is bent in accordance with the amount of pulling. Therefore, by detecting the angles of rotation as the amounts of drive of the motors $24a$ and $24b$ or pulleys $23a$ and $23b$, it is basically possible to detect the bending angle of the bending portion 11.

The present embodiment adopts a configuration in which the encoders $13a$ and $13b$ attached to the axes of rotation of the motors $24a$ and $24b$ detect the angles of rotation of the motors $24a$ and $24b$ or pulleys $23a$ and $23b$ and the bending angle of the bending portion 11 is detected from the angles of rotation of the pulleys $23a$ and $23b$. Detection signals of the encoders $13a$ and $13b$ are inputted to the drive amount detection section $15a$.

However, since the wires $12u$, $12d$, $12l$ and $12r$ (hereinafter, $12u$ or $12l$ is represented by $12a$, and $12d$ or $12r$ is represented by $12b$) involve looseness, the present embodiment removes the looseness appropriately.

Furthermore, for example, the joystick apparatus $5a$ making up the input apparatus 5 includes a joystick 26 which can be tilted arbitrarily in vertical and horizontal directions and encoders $27a$ and $27b$ that detect tilting angles of the joystick 26 in the vertical and horizontal directions respectively. The direction tilted by the joystick 26 is the bending command direction of the bending portion 11 and the tilting angle is a command value of the bending angle of the bending portion 11.

Detection signals by the encoders $27a$ and $27b$ are inputted, for example, to the control section 14 of the control apparatus. That is, the control section 14 receives command values of the bending command direction and the bending angle from the joystick apparatus $5a$ as bending command input means as input.

The control section 14 determines the angles of rotation of the motors $24a$ and $24b$ in response to the command values with reference to the information stored in the storage section 16 and drives the motors $24a$ and $24b$ to rotate so that the angles of rotation of the motors $24a$ and $24b$ detected by the encoders $13a$ and $13b$ follow the command values.

Since the wires $12a$ and $12b$ actually involve looseness, the drive force amount detection section $15b$ in the present embodiment detects the torque T of the motors $24a$ and $24b$, and the comparison section $17b$ of the correction section 17 compares the (absolute value of) torque T of the motors $24a$ and $24b$ with a positive threshold value Tth set to judge the presence or absence of looseness, and the judgment section $17a$ judges the presence or absence of looseness from the comparison result. That is, the judgment section $17a$ judges that looseness is present when the absolute value of the torque T is less than the threshold value Tth and judges that no looseness is present when the absolute value of the torque T is equal to or above the threshold value Tth.

Figure 2:
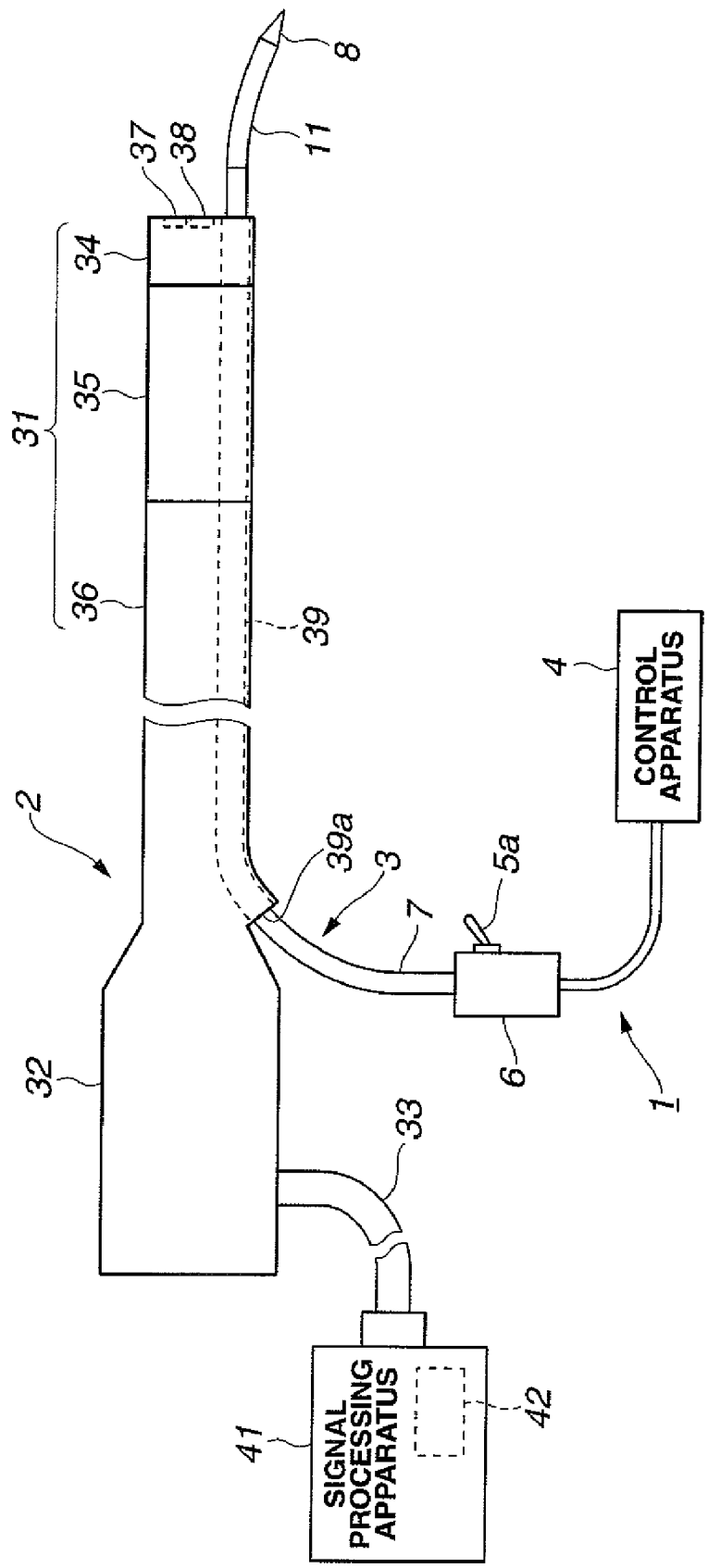
FIG. 2 is a diagram illustrating an endoscope and the treatment instrument inserted into a channel thereof.

As shown in FIG. 2, the endoscope 2 includes an insertion portion 31 inserted into the body cavity, an operation section 32 provided at a rear end of the insertion portion 31 and a universal cable 33 that extends from the operation section 32 and an end of the universal cable 33 is detachably connected to a signal processing apparatus 41.

The insertion portion 31 of the endoscope 2 includes a distal end portion 34 provided at a distal end of the insertion portion 31, a freely bendable bending portion 35 provided at a rear end of the distal end portion 34 and a flexible portion 36 that extends from a rear end of the bending portion 35 to a front end of the operation section 32.

Furthermore, the distal end portion 34 of the insertion portion 31 is provided with an illuminating window 37 that emits illuminating light and an observation window 38 formed adjacent to the illuminating window 37. Furthermore, the insertion portion 31 is also provided with the channel 39 through which the treatment instrument can be inserted and a rear end of the channel 39 opens as a treatment instrument insertion port 39a near the front end of the operation section 32. The operator such as a surgeon can insert the treatment instrument 3 from the treatment instrument insertion port 39a to perform treatment under observation with the endoscope 2.

As described above, the operation characteristic storage section 16a of the storage section 16 stores, in advance, information (data) of operation characteristics that associates an angle of rotation $\theta 1$ with a bending angle $\theta b$ as shown, for example, in FIG. 8, which will be described later.

The operation characteristic storage section 16a stores, in advance, information on operation characteristics that associates each angle of rotation $\theta 1$ with a corresponding bending angle $\theta b$ within a range in which the bending portion 11 can be bent. The information of the operation characteristics stored in the operation characteristic storage section 16a has hysteresis characteristics.

Figure 8:
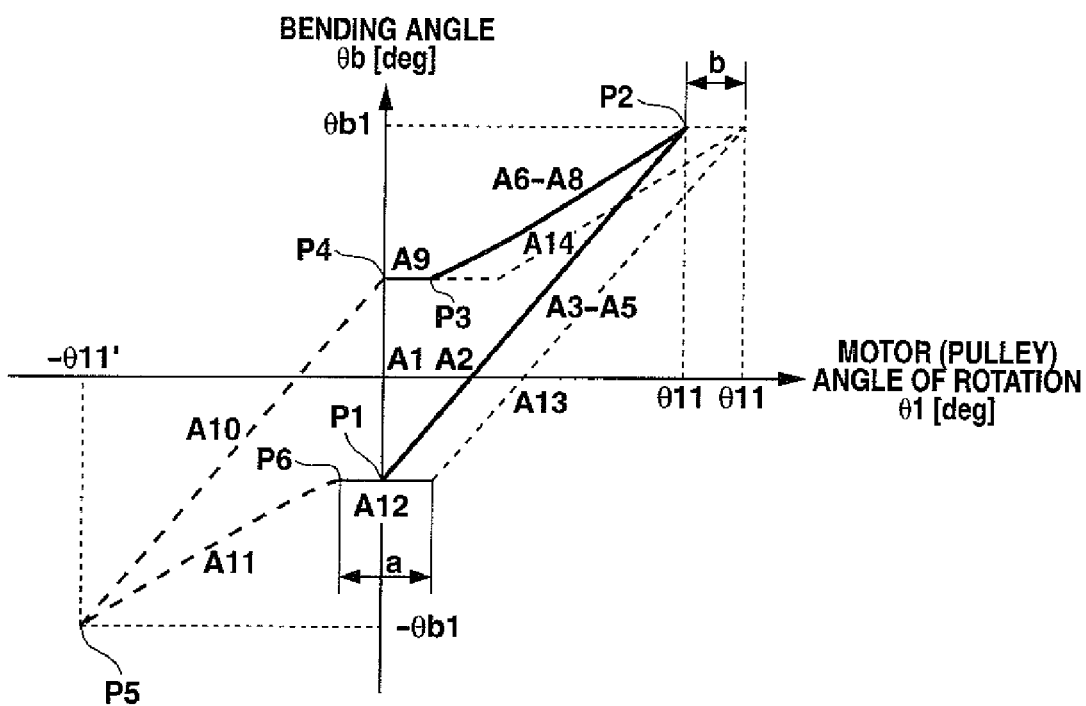
FIG. 8 is a diagram illustrating the angle of rotation and the bending angle corresponding to the case in FIG. 7.

When shown with a specific example in FIG. 8 (the horizontal axis shows an angle of rotation $\theta 1$ and the vertical axis shows a bending angle $\theta b$), this information is information (data) approximate to a diamond shape shown by coordinate positions P1 to P2 (A5), P2 to P3 (A6-A8), P4 to P5 (A10) and P5 to P6 (A11). This data does not include any portion of operation characteristics relating to looseness which varies depending on an operating environment such as portions denoted by reference numerals A1-A2, A9 and A12.

The operation characteristic storage section 16a may store information on the operation characteristic (excluding, however, the looseness portion) as shown in FIG. 8 so as to cover the range of bending angle within which the bending portion 11 can be bent or may also store operation parameters that determine such operation characteristics.

That is, the gradient of the bending angle $\theta b$ with respect to the angle of rotation $\theta 1$ denoted by reference numerals P1 to P2 (A3-A5) in FIG. 8, likewise the gradient denoted by reference numerals P4 to P5 A10, reference numerals P2 to P3 (A6-A8) as operation characteristic portions by a restoring force or the like, and reference numerals P5 to P6 (A11) or the like may be stored as information on operation parameters.

In the present embodiment, when the bending portion 11 is bent up to a predetermined angle and then bent in the opposite direction, the operation characteristic storage section 16a that forms storing means stores, in advance, information on the operation characteristics that the bending portion 11 acts to return in the opposite direction (that is, acting to restore) as reference information (to be more specific, denoted by reference numerals P2 to P3 (A6-A8) and reference numerals P5 to P6 (A11) in the example in FIG. 8) and the bending amount detection section 15 detects the corresponding bending angle from the angle of rotation of the motor through estimation with reference to the reference information.

Thus, the present embodiment stores the reference information in advance, and can thereby accurately detect (estimate) the bending angle from the angle of rotation of the motor even with a configuration without including any sensor that detects the bending angle compared to the prior art that does not store such reference information.

In addition, the operation characteristic storage section 16a also stores information on a correlation between the torque T and the bending angle $\theta b$ and information on the threshold value Tth used to judge looseness.

Due to looseness of the wires 12a and 12b, the angle of rotation $\theta 1$ and bending angle $\theta b$ actually deviate from the operation characteristics stored in the operation characteristic storage section 16a depending on the operation situation, and therefore the present embodiment judges the presence or absence of looseness and changes the information on the operation characteristics used to drive the bending when looseness is detected.

For example, suppose a command for driving the bending is inputted so as to cause the motors 24a and 24b to reciprocate the bending portion 11 in a predetermined direction and in the opposite direction. When the control section 14 drives the motors 24a and 24b to rotate in response to the command input, due to looseness of the wires 12a and 12b, the angle of rotation $\theta 1$ and the bending angle $\theta b$ of the motors 24a and 24b change as denoted by reference numeral A1 to reference numeral A2, and further reference numeral A3-A5, . . . A12, A13 in FIG. 8.

As a result, the angle of rotation $\theta 1$ is deviated, for example, in the horizontal direction by an amount of angle of rotation denoted by a generated by a portion denoted by reference numeral A12 in FIG. 8 and by an amount of angle of rotation denoted by b and the information on the operation characteristic is changed so as to shift, for example, in the horizontal direction in accordance with the deviation. Even in the case with such hysteresis characteristics where the operation characteristics vary depending on past operation states, the information of the operation characteristics is changed so as to be operation characteristics corresponding to the hysteresis characteristics.

Figure 6:
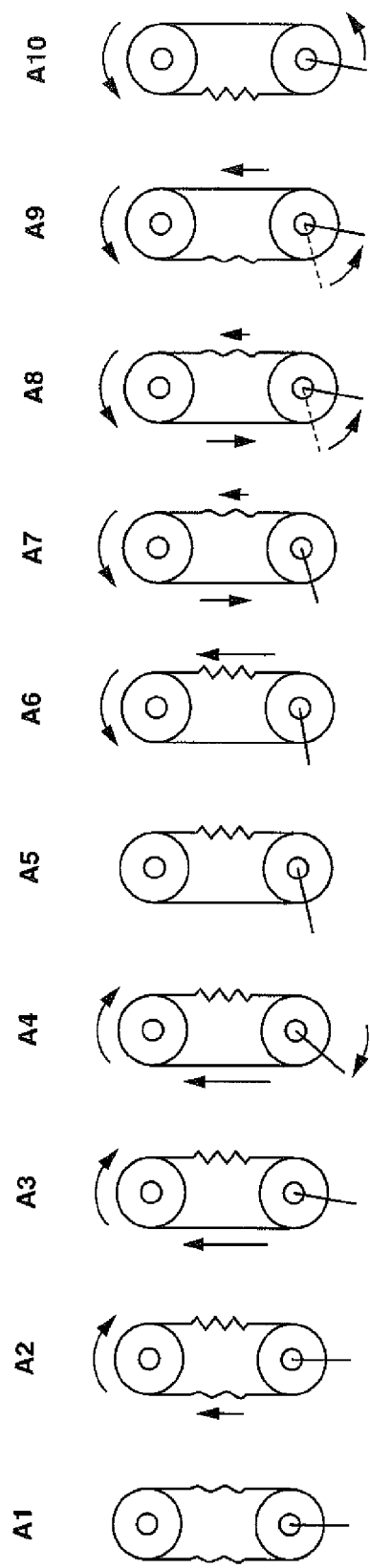
FIG. 6 is a diagram illustrating representative bent states when the bending portion is driven to bend by rotating a motor using the model in FIG. 5.

FIG. 6 shows representative bending angle states denoted by reference numerals A1, . . . A13, A14 in FIG. 8. FIG. 6 shows reference numerals A1, . . . A10.

Next, operations of the present embodiment will be described with reference to FIG. 4. When the power to the treatment instrument apparatus 1 is turned on and the control apparatus 4 starts to operate, initial setting processing in step S1 starts. In this step S1, the control apparatus 4 sets a state in which the axial section 7 of the treatment instrument 3 is straight, that is, a neutral state in which the bending portion 11 is not bent, and the angle of rotation $\theta 1$ in the vertical direction and horizontal direction and the bending angle $\theta b$ of the bending portion 11 detected by the encoders 13a and 13b of the motors 24a and 24b are set to 0. Then, the system is placed on standby waiting for a command input.

In step S2, the operator inputs a bending command from the input apparatus 5. To be more specific, the operator operates the joystick 26 to tilt the bending portion by a desired bending angle in a desired direction of bending.

As shown in step S3, in response to the bending direction and the bending angle of the command input, the control section 14 of the control apparatus 4 calculates the rotation direction (drive direction) for rotating the motors 24a and 24b (hereinafter, represented by reference numeral "24"), the torque (amount of drive force) and the angle of rotation (amount of drive) with reference to information on the operation characteristics of the storage section 16 at that time (operation state).

Figure 4:
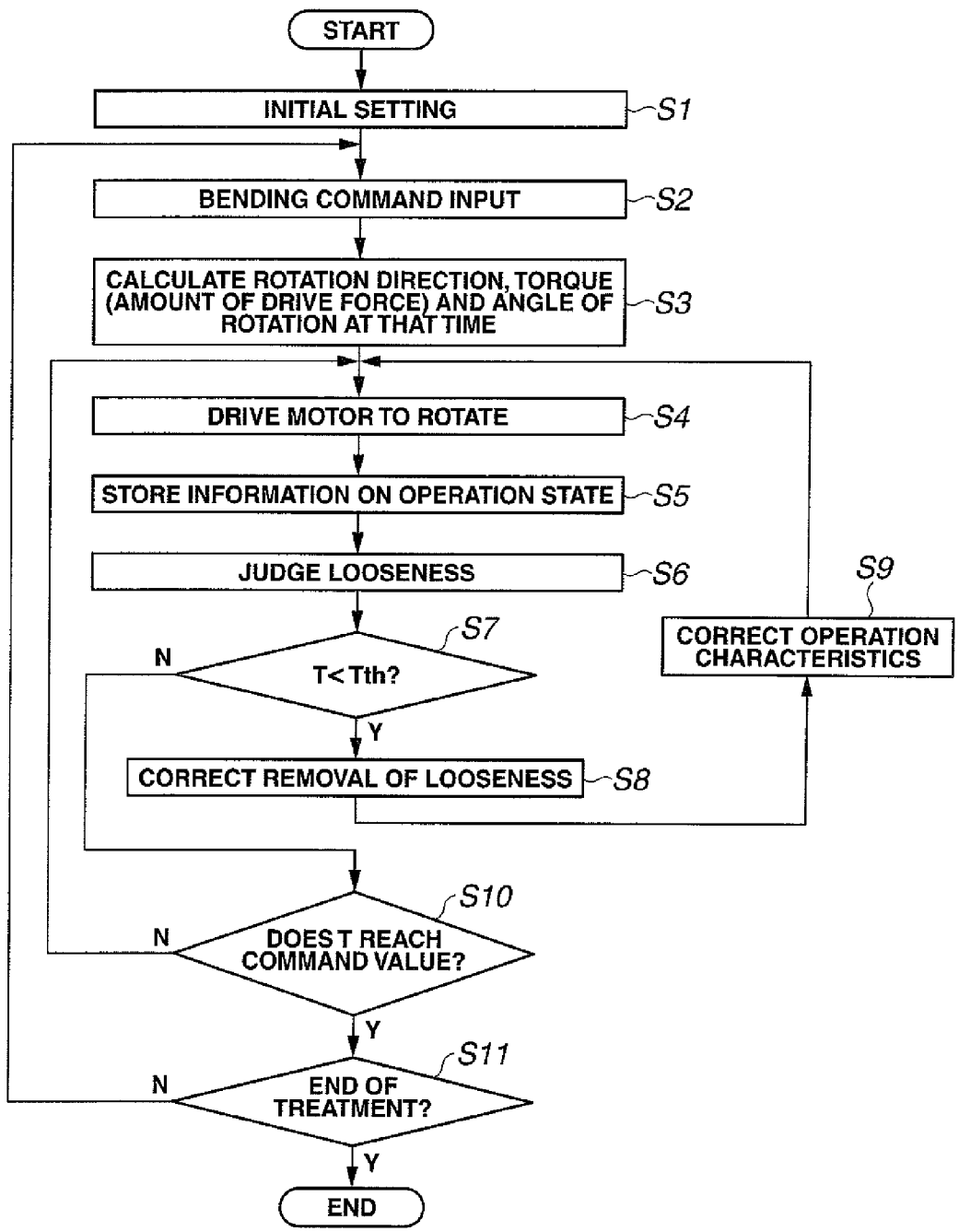
FIG. 4 is a flowchart illustrating an example of control procedure for driving the bending of the bending portion according to the first embodiment.

Though the time (operation state) is currently an initial state, a bending command is inputted from an operation state which is different from the initial state through a control loop in FIG. 4. In such a case, the rotation direction, the torque and the angle of rotation are calculated with reference to the information on the operation characteristics corrected before the operation state. The calculated torque and angle of rotation are command values or target values when driving the bending.

In next step S4, the control section 14 drives the motor 24 to rotate so as to obtain the calculated torque and angle of rotation. Furthermore, as shown in step S5, the correction section 17 monitors the operation state of the motor 24 making up the drive section 9, for example, in a fixed cycle and stores information on the operation state in the state storage section 16b.

Furthermore, as shown in step S6, the correction section 17 also judges the presence or absence of looseness. To be more specific, as shown in step S7, the comparison section 17b makes a comparison to judge whether or not the absolute value of the torque T detected by the drive force amount detection section 15b is less than a positive threshold value Tth (Tth>0).

When the judgment result shows that the absolute value of the torque T is less than the threshold value Tth, that is, the judgment result shows that looseness is present, a correction to remove the looseness is made in step S8. To be more specific, the correction section 17 drives the motor 24 to rotate as is via the control section 14. This causes a correction to be made so as to remove the looseness, and when the looseness is removed, the absolute value of the torque T becomes equal to or above threshold value Tth.

Furthermore, in step S9, the correction section 17 corrects the information on the operation characteristics referenced from the operation characteristic storage section 16a by the angle of rotation corresponding to the rotation to remove the looseness in step S8 with respect to the value of the angle of rotation calculated in step S3. This correction can be performed with high accuracy by referencing the information stored on a time-series basis in step S5.

The process then returns to the processing in step S4. In this way, when looseness is present, the correction section 17 performs drive control so as to remove the looseness and corrects (changes) the information on the operation characteristics by an amount corresponding to the looseness. In this case, since information on the operation state is stored on a time-series basis in step S5, a correction can be reliably made at each time.

When the looseness is removed in this way, the (absolute value of) torque T changes as the motor 24 rotates, and when the torque T exceeds the threshold value Tth, the process advances from step S7 to step S10. In this step S10, the correction section 17 judges whether or not the detected torque T reaches the command value, that is, the torque calculated in step S3.

When the detected torque T does not reach the command value, the process returns to the processing in step S4. On the other hand, when the detected torque T reaches the torque of the command value, the process advances to the processing in step S11 and the control section 14 judges whether or not a command for ending the treatment using the treatment instrument 3 is inputted in this step S11.

When the command for ending the treatment is not inputted, the process returns to the processing in step S2 and performs processing corresponding to the next bending command input. On the other hand, when the command for ending the treatment is inputted, the processing in FIG. 4 ends.

Since the present embodiment performs such control processing, even when looseness occurs in the wires 12a and 12b, the looseness is appropriately judged through a comparison and judgment using the threshold value Tth of the torque T and the looseness is removed, and even when the actual operation characteristics are different from the predetermined operation characteristics due to the looseness, the operation characteristics are time-sequentially corrected.

Therefore, according to the present embodiment, even when the angle of rotation of the motor 24 is affected by looseness, the influence can also be appropriately corrected and the bending portion 11 can be accurately driven to bend. Furthermore, the present embodiment is widely applicable even when there is no sensor that detects the bending angle of the bending portion 11.

Figure 5:
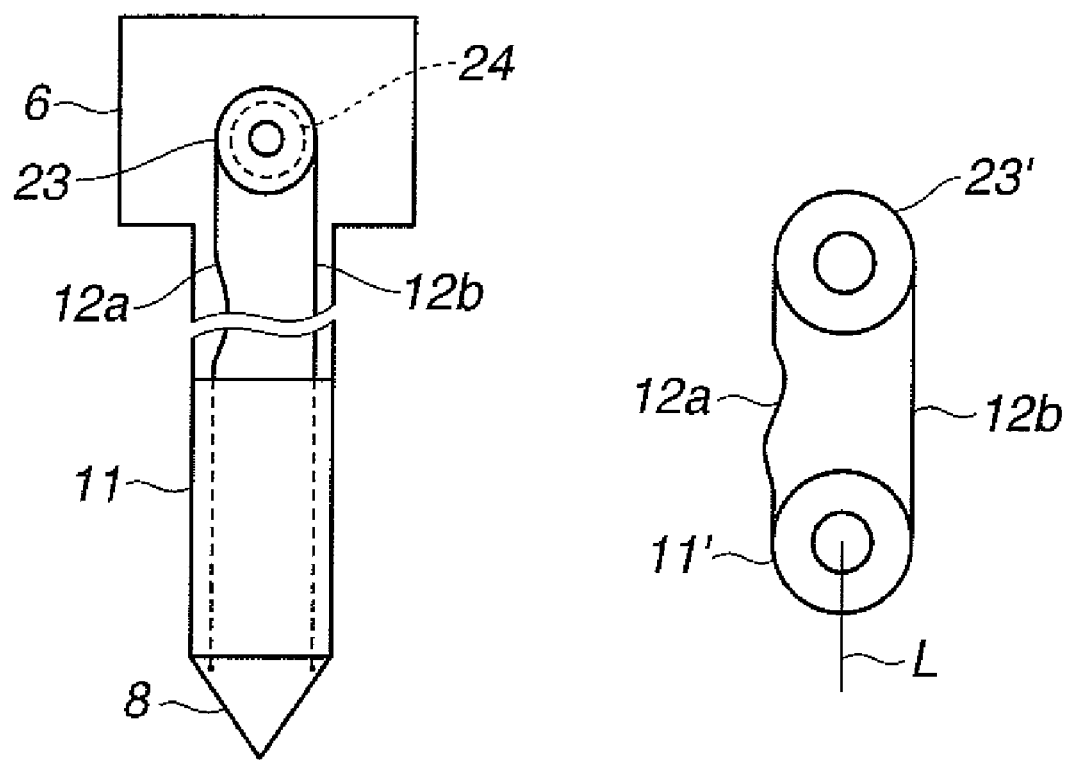
FIG. 5 is a diagram illustrating a model that simplifies the drive section and the bending portion or the like of the treatment instrument.

Next, operations of the present embodiment will be described more specifically. In this case, to illustrate the operation of the bending portion 11 in a simplified way, the drive section 9 side and the bending portion 11 side on the left side of FIG. 5 are shown as a model on the right side. On the left side of FIG. 5, one of the pulleys 23a and 23b and one of the motors 24a and 24b in FIG. 3 are represented by a pulley 23 and a motor 24 respectively.

Furthermore, the wires 12a and 12b represent the wires 12u, 12d and the wires 12l, 12r.

As shown in the model on the right side of FIG. 5, the pulley 23 on the drive section 9 side is represented by a pulley 23', the actual bending portion 11 is represented by a bending pulley 11' in a virtual form and the bending direction of the bending portion 11 is represented by a bending direction line L using a thick line.

FIG. 6 illustrates representative bending states using reference numerals A1 to A10 when repeating operations of driving the motor 24 in FIG. 5 to rotate, rotating the pulley 23 by a predetermined angle with a predetermined output and then rotating the pulley 23 by a predetermined angle in the opposite direction.

Figure 7:
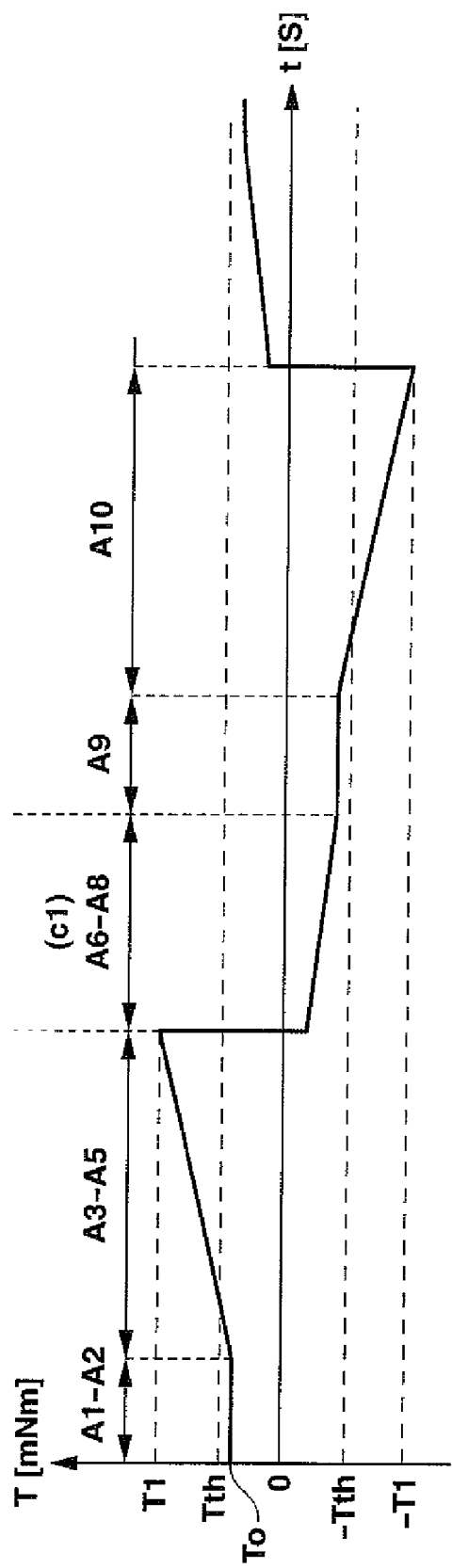
FIG. 7 is a diagram illustrating a time variation of torque when the motor is rotated using the model in FIG. 5 to repeat operations of driving the bending of the bending portion up to one bending angle and then driving the bending up to a bending angle in the opposite direction.

Furthermore, FIG. 7 illustrates torque T generated when the motor 24 pulls the wires 12a and 12b during the above described operation. Furthermore, FIG. 8 illustrates an example of the actual operation characteristics with the angle of rotation θ1 and the bending angle θb corresponding to this operation.

Reference numeral A1 in FIG. 6 shows a bending state (initial state in which the bending portion 11 is not bent, but straight) when the operation starts, and suppose the pulley 23 is rotated clockwise through the motor 24 from the state of this reference numeral A1 as denoted by reference numeral A2. At reference numeral A1, the wire 12a has looseness. Therefore, when the pulley 23 is rotated clockwise by the motor 24, the looseness of the wire 12a is removed.

That is, as shown in FIG. 7 and FIG. 8, in the process denoted by reference numeral A1-A2 where the process moves from reference numeral A1 to reference numeral A2, there is no change in the bending angle θb with respect to the angle of rotation θ1. In FIG. 7, To represents a torque value when the pulley 23 is driven to rotate with a certain output. Furthermore, T1 represents a torque value corresponding to the bending angle of a command value.

The comparison section 17b performs an operation of comparing the detected torque T with a threshold value Tth, the judgment section 17a judges that looseness is present from the comparison result T<Tth and causes the motor 24 to rotate so as to remove the looseness.

After reaching a state denoted by reference numeral A2 in which the looseness is removed, if the motor 24 further rotates, the bending angle θb also starts to change. The position of the actual operation characteristics (angle of rotation) of this reference numeral A2 is detected by the encoder 13. Furthermore, when reference numeral A2 is past, the torque T increases from the torque To of initial reference numeral A1 and when the torque T exceeds the threshold value Tth, the judgment section 17a judges that the looseness is removed.

After that, the bending angle θb also changes in accordance with the angle of rotation θ1 of the motor 24, passes through reference numerals A3 and A4, that is, passes through the process of reference numeral A3-A5 in FIG. 7 and reaches a predetermined bending angle θb1 of reference numeral A5 (coordinate position P2). The angle of rotation in this case is, for example, θ11. Furthermore, the torque T becomes torque T1 (FIG. 7) set in correspondence with the bending angle θb1.

After this, if a command input corresponding to a bending angle of −θb1 in the opposite direction is performed, the motor 24 starts to rotate in the opposite direction. In this case, as shown in FIG. 6, the wire 12b reaches a state with considerably accumulated looseness as denoted by reference numeral A5, a restoring force to restore straightness (from the bent state) is generated from an elastic member such as external tube making up the flexible axial section 7, and this restoring force causes the bending portion 11 in a bent state to act so as to decrease the bending angle θb. Furthermore, since the wires 12a and 12b are inserted into the axial section 7, frictional forces applying to the wires 12a and 12b also act.

For this reason, under the characteristics corresponding to the state in which the restoring force and frictional forces are mixed, the angle of rotation θ1 and the bending angle θb change with the characteristics denoted by reference numerals A6 to A8 in FIG. 7 and FIG. 8. The value of the bending angle θb with respect to the variation in the angle of rotation θ1 is estimated with reference to the information of the operation characteristic storage section 16a.

When the process shifts as A6-A8, since the influence of the restoring force is large at the beginning, the torque T changes from a state in which the absolute value is smaller than the value of the initial value To toward the initial value To as shown in FIG. 7.

When the restoring force balances with the frictional forces, the process reaches a state denoted by reference numeral A8 in which the influences of the restoring force substantially disappear. If looseness is present even in this sate of reference numeral A8, the bending angle θb does not change until the looseness disappears, that is, even if the angle of rotation θ1 of the motor 24 changes as reference numeral A9.

When the state of reference numeral A9 ends, the bending angle θb changes as the angle of rotation θ1 changes, and the absolute value of the torque T also exceeds the threshold value Tth. The portion of the angle of rotation denoted by reference numeral A9 where the torque T falls below the threshold value Tth is corrected as looseness.

When the absolute value of the torque T exceeds the threshold value Tth, it is judged that looseness is removed and the bending angle θ1 changes as denoted by reference numeral A10 as the angle of rotation θ1 changes. Thus, the angle of rotation θ1 and the bending angle θb change with a gradient as denoted by reference numeral A10.

Reference numeral A10 corresponds to aforementioned reference numeral A3-A5. When the bending angle reaches −θb1, the motor 24 stops rotating. In this case, the angle of rotation becomes −θ11'.

When a command input corresponding to a bending angle of θb1 continues to be performed, looseness is removed as denoted by reference numeral A12 corresponding to reference numeral A9 after passing through the process of reference numeral A11 corresponding to reference numeral A6-A8. Furthermore, the portion corresponding to this looseness is corrected.

Then, the bending angle reaches θb1 after passing through the process of reference numeral A13 shown by a dotted line corresponding to reference numeral A3-A5. In this case, the angle of rotation θ12 takes a value shifted by b from the value in the case of reference numeral A3-A5. The operation characteristics used to drive the bending is changed by the shift value. When the motor 24 is further rotated in the opposite direction, a similar process is repeated after passing through the process of reference numeral A14 shown by a dotted line in FIG. 8.

In the present embodiment, as described above, the operation characteristic storage section 16a of the storage section 16 stores information on the operation characteristics (corresponding to hysteresis characteristics) that associate the angle of rotation θ1 with the bending angle θb as shown in FIG. 8 and the operation characteristics that associates the torque T (not shown) with the bending angle θb, performs drive control, when looseness occurs in the wires 12a and 12b, so as to remove the looseness and corrects the information on the operation characteristics used to drive the bending with influences of the portion corresponding to the looseness taken into consideration.

Therefore, according to the present embodiment, even when looseness occurs, it is possible to eliminate or sufficiently reduce the influences and accurately drive the bending portion 11 to bend.

Furthermore, the present embodiment does not require any sensor for detecting tension that acts on the wires 12a and 12b and is therefore widely applicable to existing treatment instruments not provided with such a sensor.

As the information of the operation characteristics stored beforehand in the operation characteristic storage section 16a, when, for example, the axial section 7 is driven to bend from an initial straight state, the amount of looseness in that case is virtually a defined value. Therefore, the amount of looseness in that case may be stored beforehand as the information of the operation characteristics and may be treated as being different from looseness in the cases of other operation states.

Second Embodiment

Figure 9:
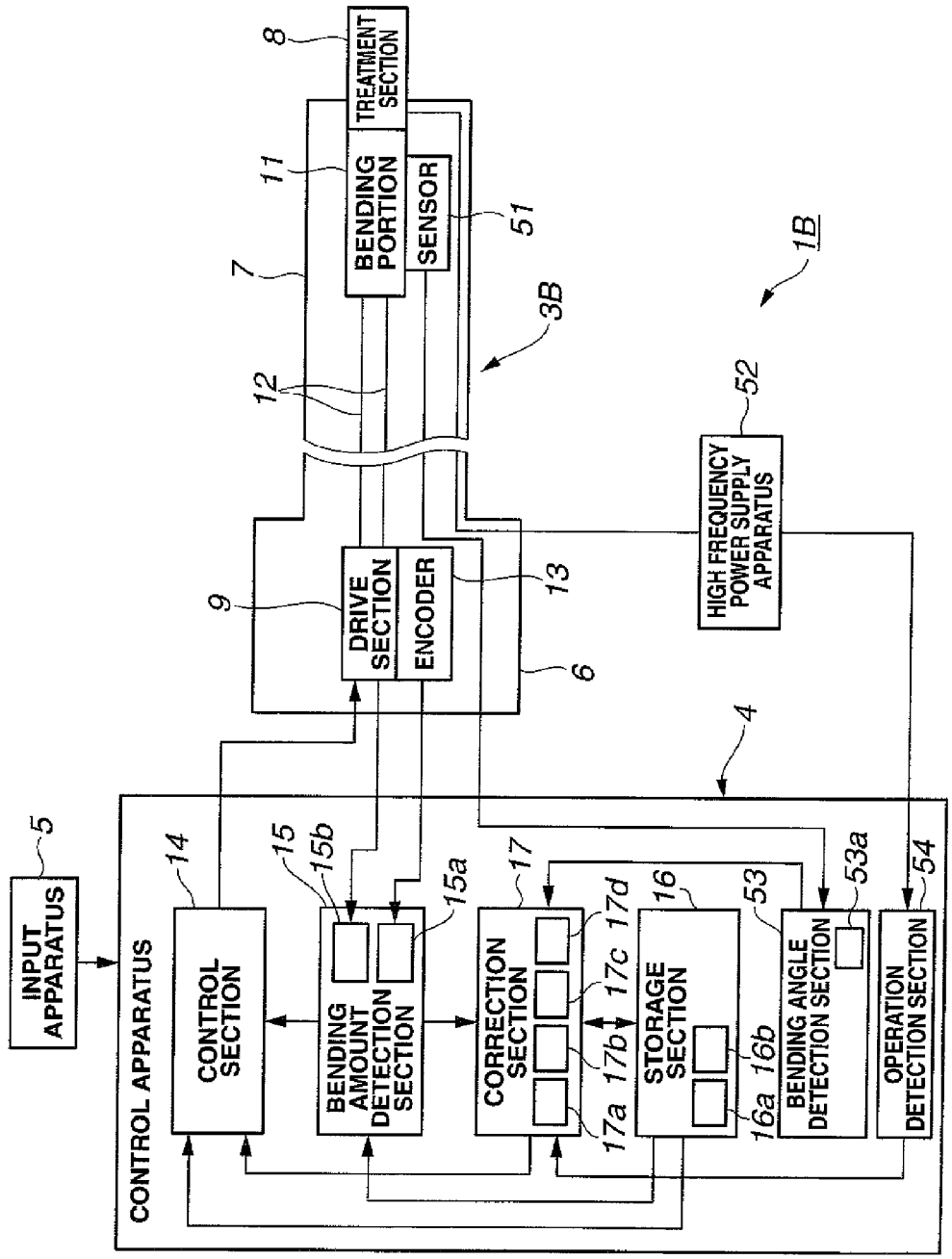
FIG. 9 is a block diagram illustrating a configuration of a treatment instrument apparatus according to a second embodiment of the present invention.

FIG. 9 illustrates a treatment instrument apparatus 1B according to a second embodiment of the present invention. The treatment instrument apparatus 1B includes a treatment instrument 3B provided with a sensor 51 in contrast to the treatment instrument 3 of the treatment instrument apparatus 1 in FIG. 1. Furthermore, the treatment instrument 3B includes a treatment section 8B that performs treatment such as removal of diseased tissue using high frequency energy of a high frequency drive signal outputted from a high frequency power supply apparatus 52 instead of the treatment section 8 of the treatment instrument 3 in FIG. 1.

Furthermore, in contrast to the control apparatus 4 of the treatment instrument apparatus 1 in FIG. 1, the treatment instrument apparatus 1B includes a control apparatus 4B provided with a bending angle detection section 53 that detects a bending angle when the detection signal of the sensor 51 is inputted and the bending angle detection section 53 outputs information on the detected bending angle to the correction section 17.

The bending angle detection section 53 includes a variable acquisition timing section 53a that makes variable a timing of acquiring a detection signal of the sensor 51.

Furthermore, a power ON/OFF state of the high frequency power supply apparatus 52 and an operation state including an output value such as high frequency output value are detected by an operation detection section 54 and the operation detection section 54 outputs the detected operation detection signal to the correction section 17.

The correction section 17 corrects an operation including an amount of drive when actually driving a bending portion 11 to bend from a detection signal by an encoder 13 and a detection signal of the bending angle by the sensor 51 according to this operation detection signal and the operation state in which the bending portion 11 is driven to bend.

While the first embodiment has a configuration including no sensor as detection means for detecting the bending angle of the bending portion 11, the present embodiment includes the sensor 51 that detects the bending angle as an amount of displacement of the bending portion 11, and therefore the present embodiment uses the detection signal of the sensor 51 to control the bending drive of the motor 24 which constitutes a drive section 9.

The present embodiment also basically performs control processing according to the flowchart shown in FIG. 4. In this case, using the detection signal of the sensor 51 that detects the bending angle, it is possible to drive the bending portion 11 to bend more accurately than in the first embodiment. In the present embodiment, the detection accuracy of the encoder 13 is set to be higher than the detection accuracy of the sensor 51.

Therefore, for example, a setting section 17c provided in the correction section 17 makes a setting such that the detection signal of the encoder 13 takes precedence over the detection signal of the sensor 51 in a normal operation state.

On the other hand, when it is difficult to accurately detect the bending angle from the detection signal of the encoder 13 due to influences of looseness of the wires 12 and the restoring force or the like (to be more specific, when detecting the bending angle using reference information of the storage section 16 described in the first embodiment), a setting is made such that the detection signal of the sensor 51 is preferentially used.

The present embodiment appropriately sets, through the setting section 17c, which of the two detection signals of the encoder 13 and the sensor 51 is to be actually used preferentially, and can thereby perform bending drive with high accuracy.

The setting information set in the setting section 17c may be stored, for example, in a flash memory as a nonvolatile, rewritable memory and may be changed/set according to the operating condition or the like.

As described above, as in the case of the first embodiment, the present embodiment also basically drives the motor 24 to rotate based on the torque T detected from the angle of rotation by the encoder 13, the current value of the motor 24 or the like with reference to information on the operation characteristics.

A main feature of the present embodiment is to detect, in the case of an operation state in which it is difficult to detect the bending angle according to the first embodiment with high accuracy, the bending angle preferentially using a detection signal of the sensor 51 rather than detect (or estimate) the bending angle corresponding to the angle of rotation from the angle of rotation based on the encoder 13 with reference to characteristics of reference information stored beforehand. By detecting the bending angle using the sensor 51, the angle of rotation corresponding to the bending angle is corrected.

Next, a correction operation by the correction section 17 of the present embodiment will be described.

Figure 10:
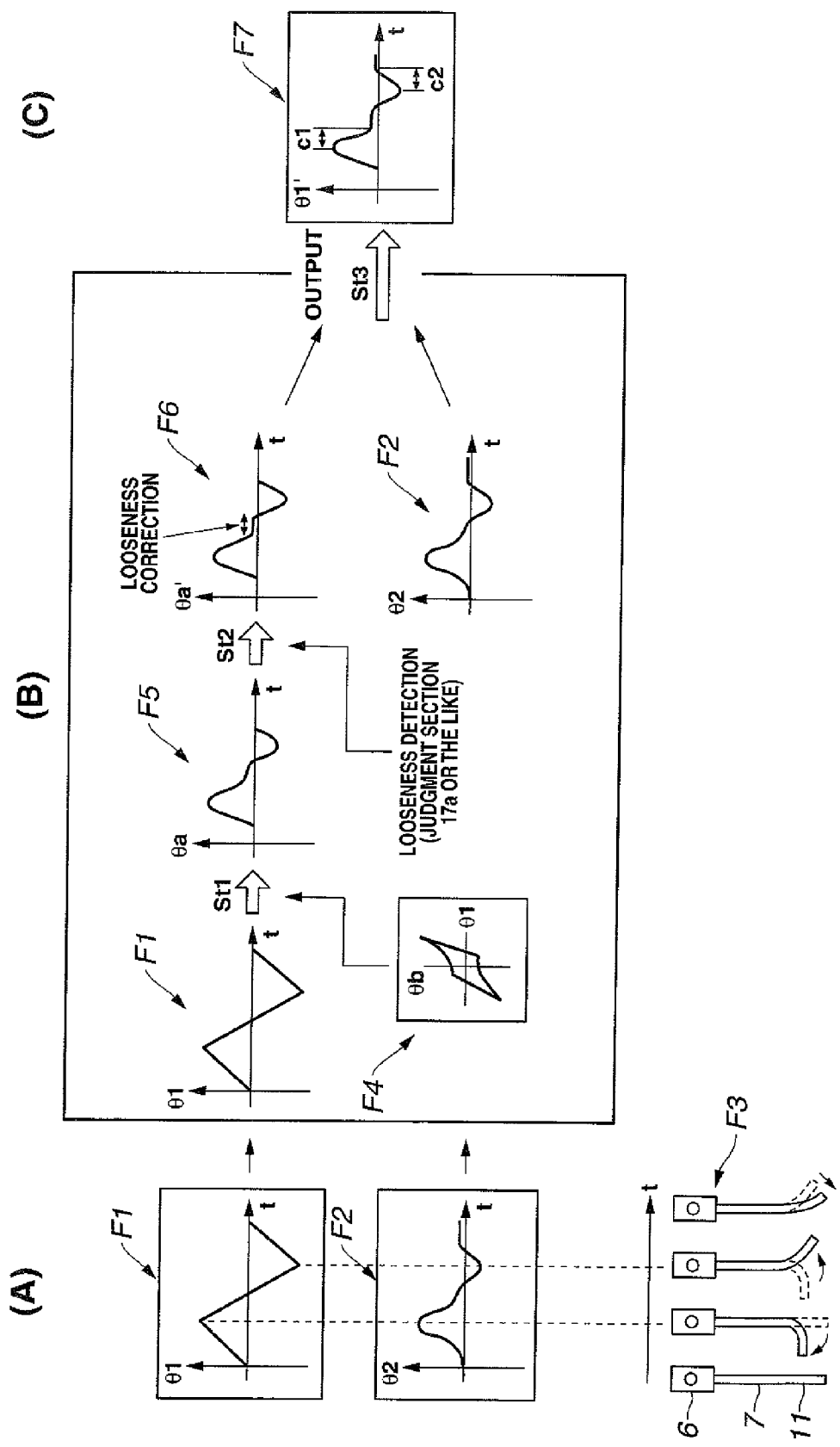
FIG. 10 is a diagram illustrating a correction operation by the correction section.

FIG. 10 is a diagram illustrating the correction operation by the correction section 17 according to the present embodiment when the motor 24 is driven to rotate based on detection signals of the encoder 13 and the sensor 51.

In the diagram illustrating the operation in FIG. 10, the correction operation before performing a correction using a detection signal of the sensor 51 is basically the same as that in the first embodiment. That is, the correction up to processes St1 and St2 in FIG. 10 is the same as that in the first embodiment and the correction in a process St3 is different from that in the first embodiment.

The figure on the bottom, third row in leftmost FIG. 10(A) of FIG. 10 denoted by reference numeral F3 illustrates a situation in which the motor 24 is driven to rotate so as to cause the bending portion 11 to perform a reciprocal bending operation such that the bending portion 11 bends by a predetermined angle leftward from a straight state and then bends by a predetermined angle in the opposite direction. Here, the horizontal axis shows a time t.

Furthermore, the figure on the first row denoted by reference numeral F1 and the figure on the second row denoted by reference numeral F2 in FIG. 10(A) illustrate the angle of rotation θ1 of the motor 24 by the encoder 13 and the bending angle θ2 detected by the sensor 51 corresponding to the case on the third row.

The angle of rotation θ1 by the encoder 13 and the bending angle θ2 by the sensor 51 are inputted to the correction section 17 via the drive amount detection section 15a and the bending angle detection section 53.

In this case, as shown in FIG. 10(B), the correction section 17 corrects the angle of rotation θ1 into an angle of rotation θa to calculate a bending angle θb of the bending portion 11 at a process St1 shown by an arrow with reference to the information of the encoder 13 denoted by reference numeral F1 and the operation characteristics (an overview of the operation characteristics thereof is denoted by reference numeral F4 in FIG. 10(B)) read from the operation characteristic storage section 16a. The characteristic of the corrected bending angle θa is denoted by reference numeral F5. When this correction is made, the information on the operation characteristics (correlation) between the bending angle θb and the torque T is also used.

The angle of rotation θa denoted by reference numeral F5 is further subjected to a looseness correction in a process St2 shown by an arrow through looseness detection by the comparison section 17b and the judgment section 17a of the correction section 17 and is transformed into an angle of rotation θa' having characteristics as denoted by reference numeral F6. The portion of the torque T whose absolute value falls below the threshold value Tth is subjected to looseness correction as denoted by reference numeral F6.

Thus, the correction section 17 compares calculated reference numeral F6 with the information of the sensor 51 denoted by reference numeral F2 and finally corrects the information into information of the angle of rotation θ' having the corrected operation characteristics in a process St3 shown by an arrow. Reference numeral F7 in FIG. 10(C) shows an example of characteristics of the angle of rotation θ' corrected in this way.

Portions denoted by reference numerals c1 and c2 of the angle of rotation θ' are corrected from, for example, the angle of rotation θa' before the correction based on the detection signal of the sensor 51. The portions denoted by reference numerals c1 and c2 are, for example, the portions denoted by reference numerals P2 to P3 (A6-A8), reference numerals P5 to P6 (A11) described as reference information in FIG. 8 in the first embodiment. Furthermore, also in FIG. 7, the portion for which the detection signal of the sensor 51 is preferentially used is shown by (c1).

In the first embodiment, it is difficult to accurately detect the bending angle θb because the restoring force or the like acts, and therefore reference information is provided beforehand to correct (complement) the accuracy, while in the present embodiment, the bending angle is directly detected using the detection signal of the sensor 51 instead of using the reference information and correct the angle of rotation with the detected bending angle. However, this is limited to a case where there is no influence of noise from a high frequency drive signal as will be described below.

Therefore, the present embodiment can perform bending drive with still higher accuracy than the first embodiment.

Furthermore, while the high frequency power supply apparatus 52 is on and high frequency energy is being outputted to the treatment section 8B, noise of a high frequency drive signal is mixed with the detection signal of the sensor 51, and therefore the present embodiment does not use the detection signal of the sensor 51. On the other hand, for a period during which high frequency energy is not being outputted to the treatment section 8B, the bending angle is reduced from an operation state of bending drive in which the bending portion 11 is, for example, bent, or when a state in which the bending portion 11 is bent in the opposite direction is detected, the detection signal of the sensor 51 is used.

That is, in the operation characteristic part of the operation characteristic storage section 16a according to the first embodiment stored as reference information, the detection accuracy of the bending angle is reduced compared to other operation characteristic parts, and therefore by detecting such an operation state and using the detection signal of the sensor 51 in that case, the detection accuracy of the bending angle improves. In this way, the drive means can improve the accuracy of driving the bending portion 11 to bend.

To realize this, for example, the correction section 17 may monitor command values of the bending direction and the bending angle inputted from the input apparatus 5 to the control section 14. Alternatively, a configuration may also be adopted in which the correction section 17 is provided with a torque variation detection section 17d (see FIG. 9) that detects a state of the drive signal from the control section 14 to the motor 24 that constitutes the drive section 9, to be more specific, a variation of the torque T which exceeds a predetermined value as an amount of drive force (as a drive force amount variation detection section).

The torque variation detection section 17d monitors such a torque variation that the absolute value of the torque T of the motor 24 varies from a large value that exceeds the threshold value Tth to a small value within a range equal to or above a predetermined value. To be more specific, the torque variation detection section 17d detects (monitors) a torque variation from a bending state of the (absolute value of) torque T which is equal to or above the threshold value Tth in a range exceeding a positive second threshold value Tth2 (>0). For example, when the rotation direction of the motor 24 changes from a state in which torque T>Tth2 in a certain rotation direction to an opposite direction, the torque variation exceeds the second threshold value Tth2.

In the case of this torque variation, that is, an operation state in which a restoring force or the like acts, the torque variation detection section 17d acquires the detection signal of the sensor 51 and corrects the operation state with the information on the bending angle detected using the detection signal.

Such control is also applied to a case where high frequency energy is not used and a case with the treatment instrument 3B using high frequency energy.

According to the present embodiment that performs such control, even in an environment where noise is likely to mix with the detection signal of the sensor 51 due to high frequency energy, it is possible to reduce the influence and realize bending drive with high accuracy. Furthermore, also when high frequency energy is not used, it is possible to appropriately use information of the sensor 51 and realize bending drive with high accuracy.

A case has been described in the aforementioned embodiments where the treatment instrument apparatus 1 or 1B provided with the treatment instrument 3 or 3B is used as a medical apparatus, but the present invention is likewise applicable to the endoscope 2 whose insertion portion 31 is provided with the bending portion 35 or an endoscope apparatus provided with the endoscope 2.

To be more specific, the present invention is likewise applicable by reading the axial section 7 and the treatment section 8 shown in FIG. 3 as the insertion portion 31 in FIG. 2, reading the grasping portion 6 as the operation section 32 and providing a control apparatus 42 corresponding to the control apparatus 4 (or 4B) shown by a dotted line in FIG. 2 inside the signal processing apparatus 41 to which the end of the universal cable 33 in FIG. 2 is connected. In this case, the system has such a configuration that the motors 24a and 24b, the pulleys 23a and 23b, and the encoders 13a and 13b are provided inside the operation section 32 of the endoscope 2.

The present invention is not only applicable to the treatment instruments 3 and 3B provided with the bending portion 11 but also widely applicable to a medical apparatus such as the endoscope 2 provided with the bending portion 35.

An embodiment configured, for example, by partially combining the aforementioned embodiments also belongs to the present invention.

What is claimed is:

1. A medical apparatus comprising:
    a bending portion that is bent via a pulled wire;
    a drive section that generates an amount of drive force to pull the wire;
    a detection section for detecting an amount of drive of the drive section;
    a drive force amount detection section that detects an amount of drive force of the drive section;
    a storage section that stores information including a correlation of the amount of drive force and the amount of drive of the drive section with respect to an amount of bending of the bending portion beforehand, the information showing an operation characteristic in which, when the bending portion is bent to a predetermined angle and subsequently bent in an opposite direction, the bending portion acts to be restored in the opposite direction;
    a bending amount detection section that detects the amount of bending of the bending portion based on the amount of drive and the amount of drive force, and the information stored in the storage section;
    a judgment section that judges the presence or absence of looseness of the wire from a detection result of the drive force amount detection section; and
    a correction section that corrects the amount of drive by the drive section based on a judgment result of the judgment section.

2. The medical apparatus according to claim 1, wherein the correction section drives, when the judgment section judges that looseness is present in the wire, the drive section to remove the looseness of the wire and corrects the information used to detect the amount of bending of the bending portion by at least the amount of drive corresponding to the looseness.

3. The medical apparatus according to claim 2, wherein the drive section is made up of a motor,
    the drive force amount detection section calculates a torque as the amount of drive force using information of a drive signal of the motor,
    the bending amount detection section detects the bending angle of the bending portion from an angle of rotation as an amount of drive of the motor, an absolute value T of the torque of the motor and information of the storage section, and the judgment section comprises a comparison section that compares the torque with a preset positive threshold value Tth, judges that looseness is present in the wire when T<Tth and judges that looseness is not present in the wire when T>Tth.

4. The medical apparatus according to claim 3, wherein the bending amount detection section detects the corresponding bending angle from the angle of rotation with reference to the information.

5. The medical apparatus according to claim 1, wherein the drive section is made up of a motor, the drive force amount detection section calculates a torque as the amount of drive force using information of a drive signal of the motor, the bending amount detection section detects the bending angle of the bending portion from an angle of rotation as an amount of drive of the motor, an absolute value T of the torque of the motor and information of the storage section, and the judgment section comprises a comparison section that compares the torque with a preset positive threshold value Tth, judges that looseness is present in the wire when T<Tth and judges that looseness is not present in the wire when T>Tth.

6. The medical apparatus according to claim 5, wherein the bending amount detection section detects the corresponding bending angle from the angle of rotation with reference to the information.

7. The medical apparatus according to claim 5, further comprising a sensor that detects a bending angle of the bending portion, wherein the correction section corrects the angle of rotation of the motor based on the detection signal of the sensor.

8. The medical apparatus according to claim 7, further comprising a setting section that makes a setting when preferentially using any one of a detection signal of an encoder that detects the angle of rotation of the motor making up the detection section used for a bending angle of the bending portion and a detection signal of the sensor.

9. The medical apparatus according to claim 8, further comprising a torque variation detection section that detects a variation from a state in which the absolute value T of the torque is equal to or above the threshold value Tth, in which the absolute value T of the torque decreases by a value equal to or above a second threshold value Tth2 that exceeds the threshold value Tth.

10. The medical apparatus according to claim 9, wherein when the torque variation detection section detects a variation where the absolute value T of the torque decreases by a value equal to or above a second threshold value Tth2, the setting section preferentially uses the detection signal of the sensor.

11. The medical apparatus according to claim 8, wherein in an environment in which a high frequency power supply apparatus generates a high frequency drive signal, the setting section makes a setting so that a detection signal of the sensor is not used.

12. The medical apparatus according to claim 8, wherein when the motor is driven, the storage section further stores data including the angle of rotation and the torque detected at each time on a time-series basis.

13. The medical apparatus according to claim 8, wherein the medical apparatus comprises an endoscope or a treatment instrument provided with the bending portion on a distal end side of an insertion portion that can be inserted into a body cavity.

14. The medical apparatus according to claim 5, wherein when the motor is driven, the storage section further stores data including the angle of rotation and the torque detected at each time on a time-series basis.

15. The medical apparatus according to claim 14, wherein the medical apparatus comprises an endoscope or a treatment instrument provided with the bending portion on a distal end side of an insertion portion that can be inserted into a body cavity.

16. The medical apparatus according to claim 15, wherein the detection section is made up of an encoder that detects an angle of rotation of the motor making up the drive section accommodated in an operation section provided at a rear end of the insertion portion.

17. The medical apparatus according to claim 14, wherein when the judgment section judges that looseness is present in the wire, the correction section drives the motor to rotate until there is no more looseness in the wire and corrects the information stored in the storage section used to detect the amount of bending of the bending portion by an angle of rotation corresponding to an amount the motor is driven to rotate from the state in which the looseness is present to the state in which the looseness is not present.

18. The medical apparatus according to claim 1, wherein the information of the storage section further includes a correlation of the amount of drive force and the amount of drive of the drive section with respect to the amount of bending of the bending portion which corresponds to the case where the bending portion is bent to the predetermined angle.

19. The medical apparatus according to claim 18, wherein, when the driving section is driven, the storage section further stores, on a time-series basis, data including the amount of drive and the amount of drive force detected at each time.

20. The medical apparatus according to claim 19, further comprising:

an input portion that is inputted with a command input for bending the bending portion; and a control section that acquires the amount of drive and the amount of drive force at an input time to the input portion as an operation state from the storage section, and determines a drive command signal to the drive section with reference to the operation state, a bending direction and a bending angle of the command input, and the information.

* * * * *

UNITED STATES PATENT AND TRADEMARK OFFICE
CERTIFICATE OF CORRECTION

PATENT NO. : 8,403,833 B2
APPLICATION NO. : 13/088750
DATED : March 26, 2013
INVENTOR(S) : Yoshitaka Umemoto It is certified that error appears in the above-identified patent and that said Letters Patent is hereby corrected as shown below:

In the Specification

Column 7, line 42 should read: erence numerals P4 to P5 (A10), reference numerals P2 to P3

Signed and Sealed this
Second Day of July, 2013

Teresa Stanek Rea
*Acting Director of the United States Patent and Trademark Office*